United States Patent [19]

Hauck et al.

[11] 4,241,059
[45] Dec. 23, 1980

[54] 6-[(ARYLOXY)METHYL]-2-MORPHOLINEMETHANOL DERIVATIVES AND USE THEREOF

[75] Inventors: Frederic P. Hauck, Bridgewater; Glenn A. Jacobs, Princeton, both of N.J.

[73] Assignee: E. R. Squibb & Sons, Inc., Princeton, N.J.

[21] Appl. No.: 104,493

[22] Filed: Dec. 17, 1979

[51] Int. Cl.³ .................. A61K 31/535; C07D 265/30
[52] U.S. Cl. ............................... 424/248.58; 544/174
[58] Field of Search ..................... 544/174; 424/248.58

[56] References Cited
U.S. PATENT DOCUMENTS

| 3,714,161 | 1/1973 | Mallion et al. | 544/174 |
| 4,044,131 | 8/1977 | Asselin et al. | 544/174 |

OTHER PUBLICATIONS

Greenwood et al., *J. Med. Chem.*, vol. 18, (1975) p. 573.

Primary Examiner—Henry R. Jiles
Assistant Examiner—R. W. Ramsuer
Attorney, Agent, or Firm—Lawrence S. Levinson; Burton Rodney

[57] ABSTRACT

6-[(Aryloxy)methyl]-2-morpholinemethanol derivatives are provided having the structure

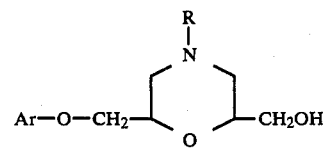

wherein R is hydrogen, lower alkyl, phenyl-lower alkyl, or lower alkenyl, and Ar represents a monocyclic or polycyclic aromatic group including tetraindiols and their analogs. These compounds are useful as adrenergic modifiers, particularly in treating arrhythmia.

12 Claims, No Drawings

6-[(ARYLOXY)METHYL]-2-MORPHOLINEMETHANOL DERIVATIVES AND USE THEREOF

DESCRIPTION OF THE INVENTION

The present invention relates to 6-[(aryloxy)methyl]-2-morpholinemethanol derivatives having the structure

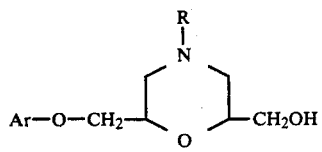

wherein R is hydrogen, lower alkyl, phenyl-lower alkyl, or lower alkenyl, and Ar is a monocyclic or polycyclic aromatic group as defined hereinafter.

The term "lower alkyl" as employed herein includes both straight and branched chain radicals of up to 8 carbons, preferably 1 to 4 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl and the like as well as such groups including a halo-substitutent, such as F, Br, Cl or I or $CF_3$ or a phenyl substituent.

The term "lower alkenyl" as employed herein includes an unsaturated hydrocarbon group having from 3 to 8 carbons and a single carbon-carbon double bond, such as ethenyl, 1-propenyl, 2-propenyl, 1-butenyl, 2-butenyl, 3-butenyl and the like.

The term "aryl" or "Ar" as employed herein refers to monocyclic or bicyclic aromatic groups containing from 6 to 10 carbons in the ring portion, such as phenyl, naphthyl, tetraindiol, substituted phenyl or substituted naphthyl wherein the substituent on either the phenyl or naphthyl may be lower alkyl, halogen (Cl, Br or F), or lower alkoxy (that is, lower alkyl-O).

Preferred are those compounds of formula I wherein R is hydrogen, methyl, ethyl or benzyl, and Ar is phenyl, or substituted phenyl, such as p-methoxyphenyl.

The compounds of formula I may be prepared by the following reaction sequence.

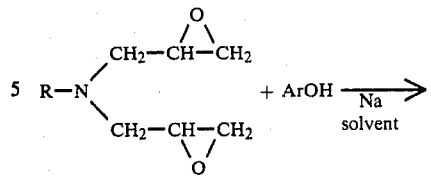

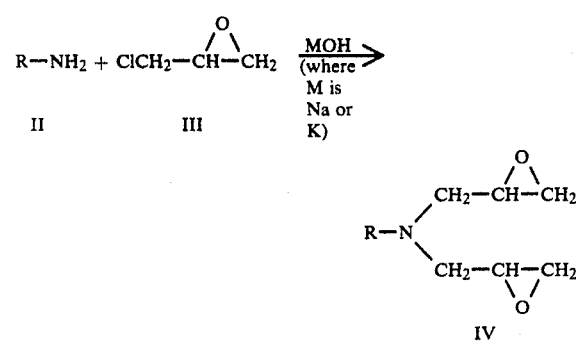

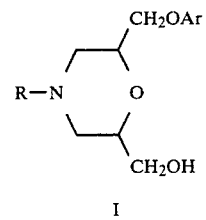

In carrying out the above reactions, the amine II is reacted with epichlorohydrin III in a molar ratio of II:III of from about 0.2:1 to about 1:1, and preferably from about 0.4:1 to about 0.8:1, at a temperature of within the range of from about 20 to about 40° C., and preferably from about 25° to about 35° C., for a period of from about 0.5 to about 8 hours or more. The reaction mixture is cooled to below room temperature, and a strong base medium, such as sodium hydroxide, is added while keeping the reaction temperature preferably below 28° C. The N,N-bis(2,3-epoxypropyl) amine IV is separated out and reacted with a mixture of compound V in an inert solvent, such as dioxane, glyme, diglyme or tetrahydrofuran, and sodium to form I. The N,N-bis(2,3-epoxypropyl)amine IV is employed in a molar ratio to compound V of within the range of from about 0.5:1 to about 1.5:1 and preferably from about 0.7:1 to about 1.2:1, and the reaction is carried out at a temperature of within the range of from about 60° to about 120° C., and preferably from about 90° to about 110° C., for a period of from about 0.5 to about 12 hours.

The compounds of formula I form acid-addition salts by reaction with various inorganic and organic acids. These salts frequently provide convenient means for separating the product from the reaction mixture in which it is produced or from the solvent in which it is extracted in view of their insolubility in various media. Thus, the product may be precipitated in the form of an insoluble salt and converted, by conventional techniques, to the free base or to another soluble or insoluble salt as desired.

Illustrative salts include the hydrohalides, such as hydrochloride, hydrobromide and hydroiodide, especially the first two, other mineral acid salts, such as phosphate, sulfate, nitrate, etc., organic acid salts, such as oxalate, tartrate, malate, maleate, citrate, pamoate, fumarate, camphosulfonate, methanesulfonate, benzenesulfonate, toluenesulfonate, salicylate, benzoate, ascorbate, mandelate, or the like.

The compounds of formula I include all stereoisomers and mixtures thereof.

The compounds of formula I have antiarrhythmic activity as indicated by the Harris coronary-ligated dog test described by A. S. Harris, Circulation 1:1318-1328, 1950 and are useful in the treatment of arrhythmia in mammalian species, for example, rats and dogs. A compound of formula I as well as its physiologically acceptable acid salts may be compounded according to pharmaceutical practice in oral or parenteral dosage forms, such as tablets, capsules, elixirs, injectables or powders for administration of about 100 mg of 400 mg per day, preferably 125 mg to 175 mg per day, in 2 to 4 divided doses.

The following Examples represent preferred embodiments of the present invention. All temperatures are expressed in degrees Centigrade.

EXAMPLE 1

6-[(4-Methoxyphenoxy)methyl]-4-(phenylmethyl)-2-morpholinemethanol

A. N,N-Bis(2,3-epoxypropyl)benzylamine

An amount of 200 g of epichlorohydrin (2.16 mole) is kept at 28°–32° while 107 g of benzyl amine (1.0 mole) is added with stirring and the reaction then maintained at 30° for 4 hours. The mixture is then cooled to 20° and 300 ml of 50% sodium hydroxide solution is added during a ½ hour period, keeping the reaction temperature between 20°–25°. The reaction is then allowed to stir for 3 hours after which time the mixture is diluted with 300 ml of water to dissolve the NaCl generated during the reaction. The upper layer is separated and washed with 100 ml of 50% NaOH, separated and vacuum distilled yielding 182 g of crude product, b.p. 186°–192° @ 0.4 mm. The crude material is then redistilled through a 10 cm Vigreux column yielding 154 g (70%) of N,N-bis(2,3-epoxypropyl)benzylamine, b.p. 188°–192° @ 0.4 mm. (Lit ref. *Houben-Weyl*, Vol. 14, Part 2, p. 544).

B. 6-[(4-Methoxyphenoxy)methyl]-4-(phenylmethyl)-2-morpholinemethanol

A solution of 6.21 g of p-methoxyphenol (0.05 mole) in 150 ml of dry dioxane is stirred under dry nitrogen and 0.4 g of finely cut sodium added. The mixture is stirred at room temperature for 1 hour and then 10.96 g of N,N-bis(2,3-epoxypropyl)benzylamine (0.05 mole) is added to the reaction mixture. The mixture is then heated at reflux for 18 hours, cooled to room temperature and poured into 300 ml of water. The aqueous mixture is extracted with 3×125 ml portions of chloroform. The CHCl$_3$ extracts are combined, washed with 200 ml of water and 200 ml of saturated NaCl solution. The CHCl$_3$ layer is then dried over anhydrous NaSO$_4$, evaporated in vacuo to yield 15.4 g (90%) of crude product as a pale yellow oil. The oil is chromatographed on 300 g of neutral Alumina III to give 11.8 g (69%) of wet product (eluted with 650 ml of chloroform and 200 ml of 2% methanolic chloroform). 11.8 g of wet product is dried in vacuo to give the desired product as a clear colorless oil.

EXAMPLES 2 to 15

Following the procedure of Example 1, except substituting for benzylamine, the amine shown in Column I of Table A below, and substituting for p-methoxyphenol, the compound shown in Column II, the product shown in Column III is obtained.

TABLE A

| Ex. No. | Column I<br>R—NH$_2$<br>R | Column II<br>ArOH<br>Ar | Column III<br>R | Ar |
|---|---|---|---|---|
| 2. | H | 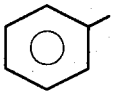 | as in Column I | as in Column II |
| 3. | H | 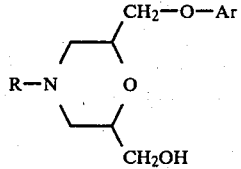 | | |
| 4. | H | 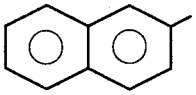 | | |
| 5. | H | 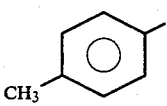 | | |
| 6. | CH$_3$ | 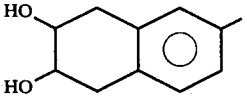 | | |

Column III structure:

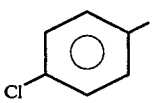

TABLE A-continued

| | Column I<br>R—NH₂ | Column II<br>ArOH | Column III<br>R—N with CH₂—O—Ar and CH₂OH branches on morpholine ring | |
|---|---|---|---|---|
| Ex.<br>No. | R | Ar | R | Ar |
| 7. | C₂H₅ | 3-OC₂H₅-phenyl | as in Column I | as in Column II |
| 8. | C₃H₇ | 1-naphthyl | | |
| 9. | C₆H₅CH₂ | 6,7-dihydroxy-1,2,3,4-tetrahydronaphth-2-yl (HO, HO on cyclohexane ring fused to benzene) | | |
| 10. | C₆H₅CH₂ | phenyl | | |
| 11. | C₆H₅CH₂ | 1-naphthyl | | |
| 12. | CH₂=CH—CH₂— | phenyl | | |
| 13. | CH₃CH=CH—CH₂— | 4-methoxyphenyl (CH₃O) | | |
| 14. | CH₃—CH=CH₂— | 2-chlorophenyl (Cl) | | |
| 15. | C₆H₅CH₂ | 3-OCH₃-phenyl | | |

EXAMPLE 16

(cis)-1,2,3,4-Tetrahydro-5-[[6-(hydroxymethyl)-2-morpholinyl]methoxy]-2,3-naphtholinediol A. N,N-Bis(2,3-epoxypropyl)butylamine benzylamine The above title A compound is prepared employing a procedure similar to that described in Houben Weyl, Vol. 14, Part 2, p. 544.

200 G of epichlorohydrin (2.16 mole) at 28°–32° is stirred and slowly 107.16 g of benzylamine (1.0 mole; d=0.981) is added with stirring and the reaction then maintained at 30° for 4 hours. The mixture is then cooled to 20° and 300 ml of 50% sodium hydroxide solution is added during a ½ hour period, keeping the reaction temperature between 20°–25°. The reaction is then allowed to stir for 3 hours after which time the mixture is diluted with 300 ml of water to dissolve the NaCl generated during the reaction. The upper layer is separated and washed with 100 ml of 50% NaOH, separated and vacuum distilled yielding 182 g of crude product, b.p. 186°–192° at 0.4 mm. The crude material is then redistilled through a 10 cm vigreux column yielding 154 g (70%) of the Title A compound, b.p. 188°–192° at 0.4 mm. I.R. and N.M.R. are consistent with the structure.

B. 4-(Phenylmethyl)-6-[[(3a,4,9,9a-tetrahydro-2,2-dimethylnaphtho[2,3-d]-1,3-dioxol-5-yl)oxy]methyl]-2-morpholinemethanol 11.01 G of cis-triolacetonide (0.05 mole) is dissolved in 100 ml of dry dioxane and then 0.3 g of finely cut sodium is added and the mixture then stirred under nitrogen for 2½ hours while the sodium is dissolved. Then the reaction is kept under a nitrogen atmosphere at room temperature while 10.96 g of N,N-bis(2,3-epoxypropyl)benzylamine (0.05 mole) is added and the resulting mixture stirred at room temperature for ½ hour. Then the reaction mixture is heated at reflux overnight under dry nitrogen atmosphere. A small amount (1 ml) of methanol is added to the mixture to destroy any excess sodium remaining. The mixture is filtered and the dioxane removed in vacuo yielding a heavy brown oil (20.6 g). This material is then chromatographed on silica gel (neutral), eluting with a mixture of 5% methanol in chloroform. The fractions are combined containing the product, and the solvent removed in vacuo yielding 10.2 g (46%) of 4-(phenylmethyl)-6-[[(3a,4,9,9a-tetrahydro-2,2-dimethylnaphtho[2,3-d]-1,3-dioxol-5-yl)oxy]-methyl]-2-morpholinemethanol.

C. 6-[[(3a,4,9,9a-Tetrahydro-2,2-dimethylnaphtho[2,3-d]-1,3-dioxol-5-yl)oxy]-methyl]-2-morpholinemethanol 4.39 G (0.01 mole) of the title B compound is dissolved in 100 ml of glacial acetic acid (anhydrous) and 4.0 g of 10% palladium on carbon is added as a catalyst. The mixture is then debenzylated over a period of 3½ hours at room temperature at a pressure of 50 psi of hydrogen. The crude mixture is filtered and the acetic acid removed in vacuo yielding 4.2 g of dark yellow oily residue. This material is chromatographed on silica gel, eluting with 10% methanol in chloroform. The fractions containing the product are combined. and the solvent removed in vacuo yielding 2.1 g (60%) of the title C compound (IR and NMR consistent with structure).

D. 1,2,3,4-Tetrahydro-5-[[6-(hydroxymethyl)-2-morpholinyl]methoxy]-2,3-naphtholinediol A portion of the title C compound is dissolved in 200 ml chloroform and is washed with 50 ml of 0.1 N hydrochloric acid. The chloroform layer is separated and washed with water, followed by a washing with saturated sodium chloride solution. The chloroform is then removed in vacuo yielding the desired product.

EXAMPLE 17

1,2,3,4-Tetrahydro-5-[[6-(hydroxymethyl)-2-(N-butylmorpholinyl)]methoxy]-2,3-naphtholinediol A. 6-[[3a,4,9,9a-Tetrahydro-2,2-dimethylnaphtho[2,3-d]-1,3-dioxol-5-yl]oxy]-methyl-2-N-butylmorpholinemethanol A portion of the title C compound of Example 16 is dissolved in dioxane and 1 equivalent of sodium is added to the mixture at room temperature. After all of the sodium has reacted, 1.1 equivalents of 1-butylbromide is added and the mixture refluxed overnight. The reaction is then cooled to room temperature, filtered, and evaporated to dryness in vacuo yielding a thick oily residue. The oily residue is separated by chromatography, silica gel, eluting with 5% methanol in chloroform, yielding the product as a pale yellow oil.

B. 1,2,3,4-Tetrahydro-5-[[6-(hydromethyl)-2-(N-butylmorpholinyl)]methoxy]-2,3-naphtholinediol A portion of the title A compound is dissolved in 200 ml chloroform and is washed with 50 ml of 0.1 N hydrochloric acid. The chloroform layer is separated and washed with water, followed by a washing with saturated sodium chloride solution. The chloroform is then removed in vacuo yielding the desired product.

EXAMPLE 18

Following the procedure of Example 17 except substituting 1-bromo-2-butene for 1-butylbromide, the corresponding 2-butenyl compound of the invention is obtained.

EXAMPLE 19

6-[(4-Methoxyphenoxy)methyl]-2-morpholinemethanol

A. 6-[(4-Methoxyphenoxy)methyl]-4-(phenylmethyl)-2-morpholinemethanol 6.21 G of p-methoxyphenol (0.05 mole Aldrich) is dissolved in 150 ml of dry dioxane and 0.4 g of finely cut sodium is added to the mixture. Stirring is continued for 1 hour after which all of the sodium is reacted with the phenol. Then 10.96 g (0.05 mole) N,N-bis(2,3-epoxypropyl)benzylamine is added and the mixture stirred for ½ hour under nitrogen. A flask is fitted with a reflux condenser and the mixture added and heated at reflux for 18 hours. After cooling to room temperature, the entire mixture is poured into 300 ml of water and stirred for ½ hour. The aqueous mixture is extracted with 3×125 ml portions of chloroform. The CHCl$_3$ extracts are combined, washed with 200 ml of water and 200 ml of saturated NaCl solution. The CHCl$_3$ layer is then dried over anhydrous NaSO$_4$ and evaporated in vacuo to yield 15.4 g (90%) of crude product as a pale yellow oil. The oil is chromatographed on 300 g of neutral Alumina III to give 11.8 g of the title A compound (69%). The 11.8 g of product is dried in vacuo to give the title A as a clear colorless oil.

B. 6-[(4-Methoxyphenoxy)methyl]-2-morpholinemethanol 3.4 G (0.01 mole) of the title A compound is dissolved in 100 ml of glacial acetic acid and 3.5 g of 10% palladium on carbon is added on a catalyst. The mixture is then debenzylated over a period of 4 hours at room temperature and under 50 psi of hydrogen. The crude mixture is filtered and the acetic acid removed in vacuo yielding 3.27 g of a yellow oil. The oily residue is distilled in vacuo (0.01 mm), the fraction distilling at 192°–194° at 0.01 mm is collected yielding 2.2 g (88%) of 6-[(4-methoxyphenoxy)methyl]-2-morpholinemethanol. Strong NH band is i.v. at 3200$^{-cm}$.

What is claimed is:

1. A compound having the structure

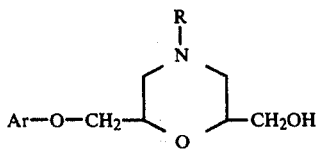

wherein R is hydrogen, lower alkyl, phenyl-lower alkyl or lower alkenyl, and Ar is a monocyclic or bicyclic aromatic ring containing from 6 to 10 carbons in the ring, and physiologically acceptable acid-addition salts thereof.

2. The compound as defined in claim 1 wherein Ar is phenyl, naphthyl, tetraindiol, phenyl substituted with one or two lower alkyl, lower alkoxy or halogen groups, or naphthyl substituted with one or two lower alkyl, lower alkoxy or halogen groups.

3. The compound as defined in claim 1 wherein R is phenyl-lower alkyl and Ar is phenyl or substituted phenyl.

4. The compound as defined in claim 1 wherein R is benzyl or hydrogen and Ar is p-methoxyphenyl.

5. The compound as defined in claim 1 wherein Ar is

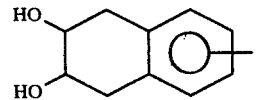

6. The compound as defined in claim 5 wherein R is hydrogen.

7. The compound as defined in claim 5 wherein R is benzyl.

8. The compound as defined in claim 5 wherein R is lower alkenyl.

9. The compound as defined in claim 5 having the name 1,2,3,4-tetrahydro-5-[[6-(hydroxymethyl)-2-morpholinyl]methoxy]-2,3-naphtholinediol.

10. The compound as defined in claim 5 having the name 1,2,3,4-tetrahydro-5-[[6-(hydroxymethyl)-2-(N-butylmorpholinyl)]methoxy]-2,3-naphtholinediol.

11. A pharmaceutical composition for use in treating arrhythmia comprising an anti-arrhythmic effective amount of a compound as defined in claim 1 and a pharmaceutically acceptable carrier therefor.

12. A method for treating arrhythmia in mammals, which comprises administering an antiarrhythmic effective amount of a compound as defined in claim 1.

* * * * *